(12) United States Patent
Lowe

(10) Patent No.: US 9,569,588 B2
(45) Date of Patent: Feb. 14, 2017

(54) ATTACHED PERSONAL INFORMATION DEVICE

(76) Inventor: John C. Lowe, Bethesda, MD (US)

( * ) Notice: Subject to any disclaimer, the term of this patent is extended or adjusted under 35 U.S.C. 154(b) by 1336 days.

(21) Appl. No.: 10/938,503

(22) Filed: Sep. 13, 2004

(65) Prior Publication Data

US 2006/0059013 A1    Mar. 16, 2006

(51) Int. Cl.
*G06Q 10/00* (2012.01)
*G06Q 50/00* (2012.01)
*G06F 19/00* (2011.01)
*G06Q 50/22* (2012.01)

(52) U.S. Cl.
CPC .............. *G06F 19/323* (2013.01); *G06Q 50/22* (2013.01)

(58) Field of Classification Search
CPC ...... G06Q 50/22–50/24; G06F 19/322–19/327
USPC ........................................... 705/2–3
See application file for complete search history.

(56) References Cited

U.S. PATENT DOCUMENTS

| | | | |
|---|---|---|---|
| 4,027,391 A * | 6/1977 | Samis | 433/229 |
| 5,867,821 A * | 2/1999 | Ballantyne et al. | 705/2 |
| 6,298,421 B1 * | 10/2001 | Minamizawa et al. | 711/151 |
| 2002/0013613 A1 * | 1/2002 | Haller et al. | 607/60 |
| 2003/0009203 A1 * | 1/2003 | Lebel et al. | 607/60 |

OTHER PUBLICATIONS

Mary H.H. Ensom, "2001: A Pharmacogenomics Odyssey", *CJHP*-vol. 54, No. 1—Spring 2001, JCPH—vol. 54, n° 1—printemps 2001. pp. 6-7.

Peter McGrath, "Technology: Building Better Humans", http://egweb.mines.edu/eggn482/admin/Technology.html, printed on Jan. 29, 2004, 3 pp., (Jan. 2001).

* cited by examiner

*Primary Examiner* — Sheetal R Paulson
(74) *Attorney, Agent, or Firm* — Snyder, Clark, Lesch & Chung, LLP

(57) ABSTRACT

An information storage device may be semi-permanently attached to a wearer. The device can include an outer casing configured to be compatible with long term contact with a human body. A data storage component may store information of the wearer and a transceiver may wirelessly communicate information from the data storage component. The stored information can be, for example, the complete medical history of the wearer, "emergency" medical information, prescriptions, medical warnings (e.g., past history of coronary problems), financial information, social security numbers, or other useful information.

32 Claims, 9 Drawing Sheets

ATTACHED PERSONAL INFORMATION DEVICE

BACKGROUND OF THE INVENTION

A. Field of the Invention

The present invention relates generally to information storage, and more particularly, to personal information storage in which the storage device is attached to the person.

B. Description of Related Art

Personal information, such as contact information and medical conditions, can provide vital information to emergency rescue or medical staff. It can thus be desirable to keep this information securely associated with the individual. One known technique for storing and making available such information uses bracelets or "dog tag" type necklaces that are worn by the individual and that contain written information. Some disadvantages associated with these devices are that they can be cumbersome, have a small information capacity, and are not very secure.

In addition to contact or medical information, it may be desirable to associate other types of personal information, such as financial information or identification information, with the individual.

Accordingly, there is a need in the art for improved devices through which an individual can carry information.

SUMMARY OF THE INVENTION

One aspect of the invention includes an information storage device designed to be semi-permanently attached to a wearer. The device includes an outer casing configured to be compatible with long term contact with a human body, a data storage component located within the outer casing and configured to store information of the wearer, and a transceiver located within the outer casing and configured to communicate with an external reader device.

Another aspect of the invention is a personal information storage device that includes a data storage component configured to store information of a wearer and a transceiver configured to communicate with an external reader device. The personal information storage device is embedded within a crown or false tooth of the wearer. Yet another aspect consistent with the invention is directed to a method of providing information from a storage device attached to a wearer. The method includes wirelessly receiving a request for data, authenticating the request as being authorized to access data in the storage device, and transmitting the requested data when the requests are determined to be an authorized. The storage device attached to the wearer is implemented as a subcutaneous device or as a device disposed within the oral cavity of the wearer.

BRIEF DESCRIPTION OF THE DRAWINGS

The accompanying drawings, which are incorporated in and constitute a part of this specification, illustrate an embodiment of the invention and, together with the description, explain the invention. In the drawings.

DETAILED DESCRIPTION

The following detailed description of the invention refers to the accompanying drawings. The detailed description does not limit the invention.

A personal information storage device is described herein that is "permanently" or semi-permanently attached to the individual. Examples of such attachments include a subcutaneous chip, a false tooth or crown with embedded electronic intelligence, or jewelry (e.g., an earring) with embedded electronic intelligence. The device may communicate with external reader devices to convey the personal information of the individual.

The personal information storage device may store a variety of different types of information, such as medical history, prescriptions, medical information (e.g., allergies, coronary problems, contraindications), contact information for family or emergency contacts (e.g., doctors, employer, relatives), financial information, or other useful information.

Physical Implementations

Figure 1:
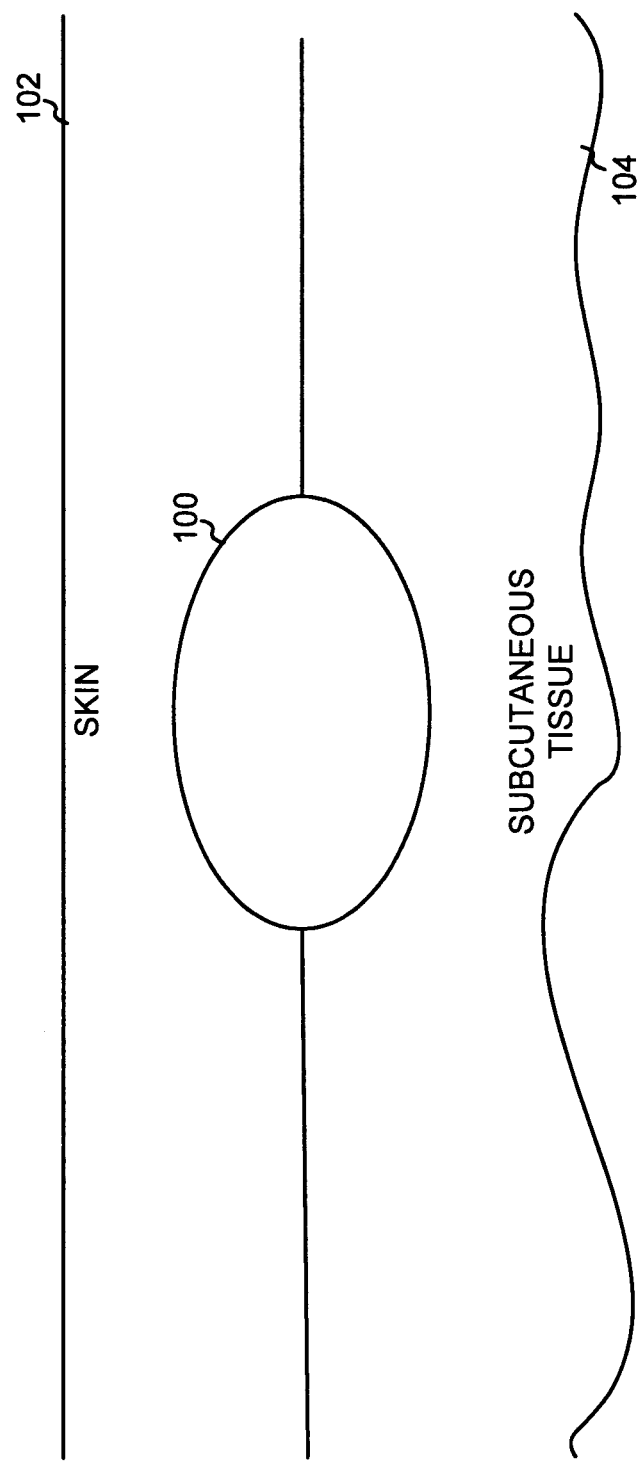
FIG. 1 is a diagram illustrating a personal information storage device according to one exemplary embodiment.

FIG. 1 is a diagram illustrating a personal information storage device 100 according to one exemplary embodiment. In this implementation, personal information storage device 100 is designed to be implanted in the body. Personal information storage device 100 may, for example, be implanted between skin 102 and subcutaneous tissue 104 of a human. Because storage device 100 is implanted within the body, the outer casing of storage device 100 should be designed to be compatible with human tissue. For example, storage device 100 may be of a size that does not interfere with bodily functions or cause pain or discomfort (e.g., if formed under the skin, it may be of a smooth, oblong or rounded shape).

Figure 2:
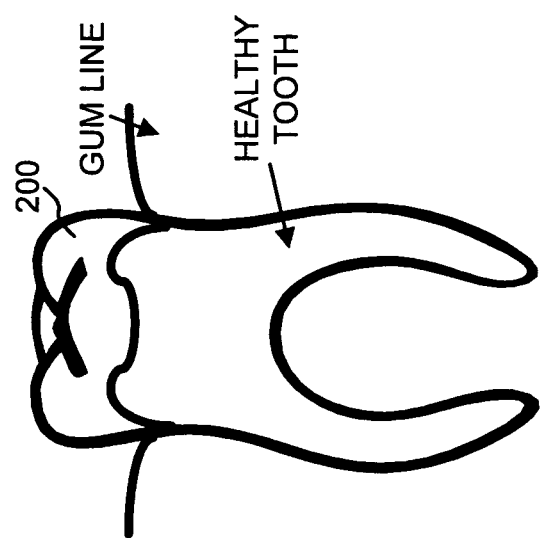
FIG. 2 is a diagram illustrating a personal information storage device according to another exemplary embodiment.

FIG. 2 is a diagram illustrating a personal information storage device 200 according to another exemplary embodiment. In this implementation, storage device is placed within the oral cavity, such as within a false tooth or as a crown. In other implementations, personal information storage device 200 may be placed on or in other artificial body attachments, such as in a prosthetic limb. In particular, as shown in FIG. 2, personal information storage device 200 may be designed to be embedded in a crown, or a portion of a crown or false tooth. The outer casing of storage device 200 may thus be an enamel like material. In some implementations, personal information storage device 200 may be designed such that it can be repeatedly removed and re-inserted by the wearer via, for example, removable dental epoxy or a locking mechanism at the base of the storage device.

As discussed above with reference to FIGS. 1 and 2, personal storage devices are shown that are tightly integrated with the individual ("wearer") with which they are associated. Thus, they may be installed or worn throughout the day and night without interfering with the normal activities of the individual. In essence, they may essentially be considered to be "permanent" or semi-permanent devices associated with the wearer.

Figure 3:
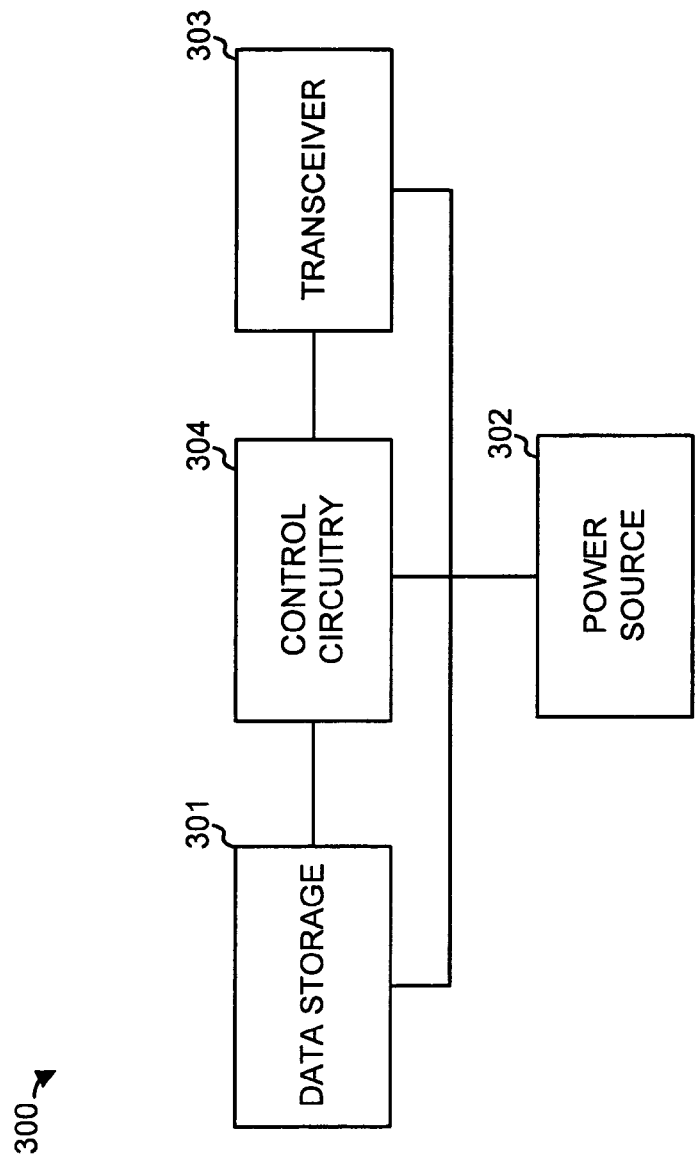
FIG. 3 is a block diagram illustrating exemplary functional features of the personal information storage devices of FIGS. 1 and 2.

FIG. 3 is a block diagram illustrating exemplary functional features of personal information storage devices 100 and 200. Personal information storage devices 100 and 200 will collectively be referred to as personal information storage device 300 herein. Device 300 may include a data storage component 301, a power source 302, a transceiver 303, and control circuitry 304.

Data storage component 301 may include mechanisms for storing the data of the wearer and may be implemented using a number of different possible storage technologies. For example, storage technologies based on magnetic, optical, semiconductor solid state, or hardwired storage may be used. In some implementations, data storage component 301 may be a read-only component in which the stored data is externally pre-programmed. Applications in which data storage component 301 stores non-changing information, such as medical allergy information or personal identification information, such as social security numbers, may be particularly suited to this implementation. In other implementations, data storage component 301 may include read/write functionality in which data can be dynamically written to and read from data storage component 301.

Power source 302 may provide power to data storage component 301, transceiver 303, and/or control circuitry 304. In one implementation, power source 302 may include a battery or some other source of long term stored energy. In other implementations, power source 302 may include an inductor designed to generate power when in the presence of electromagnetic radiation. In these implementations, an external reader may generate and expose power source 302 to a field of electromagnetic radiation, causing power source 302 to generate electric power. In still other implementations, power source may include other mechanisms for generating power, such as a solar cell or via a mechanism that converts energy associated with the wearer (e.g., motion of the wearer) to electric power.

Transceiver 303 may send, and in some implementations, also receive information from external sources. Transceiver 303 may include, for example, an antenna that is used to wirelessly transmit and/or receive information. In other implementations, transceiver 303 may additionally include a port for receiving/transmitting information via a wired connection. In still other possible implementations, transceiver may communicate through optical or infra-red connections.

Control circuitry 304 provides the "intelligence" of personal information storage device 300. Control circuitry 304 may, for example, read data from data storage component 301 and transmit the data using transceiver 303. Similarly, in some implementations, control circuitry may control the receiving of information via transceiver 303 and process the information and/or write it to data storage component 301. One of ordinary skill in the art will recognize that control circuitry 304 can provide a number of other functions, such as providing password based security for the information stored by personal information storage device 300.

When communicating wirelessly using an antenna in transceiver 303, personal information storage device 300 may communicate via a number of possible communication protocols, ranging from a relatively simple custom protocol to more complicated protocols, such as the known Bluetooth or the IEEE 802.11 (WiFi) series of protocols.

Operation of Personal Information Storage Device
in Reading/Writing Information

Figure 4:
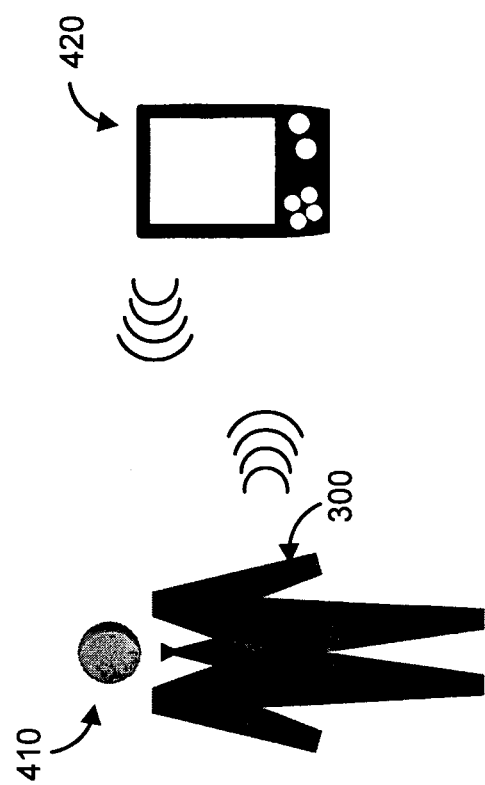
FIG. 4 is a diagram illustrating an exemplary system through which a personal information storage device may be used.

FIG. 4 is a diagram illustrating an exemplary system through which personal information storage device 300 may be used. As shown, personal information storage device 300 may be associated with a wearer 410, for example, as an embedded subcutaneous chip. A reader device 420 may be used to communicate with personal information storage device 300. Reader device 420 may be implemented in many different configurations, such as, for example, a small portable device, a device connected to or integrated within a point of sale terminal, or as a device connected to or integrated within a computer system in an office environment. As illustrated in FIG. 4, reader device 420 is implemented as a portable computer device. Reader device 420 may include antennae (not shown) for wirelessly transmitting data signals or power signals to personal information storage device 300. Additional or the same antennae may also be used to receive communications from personal information storage device 300.

Figure 5:
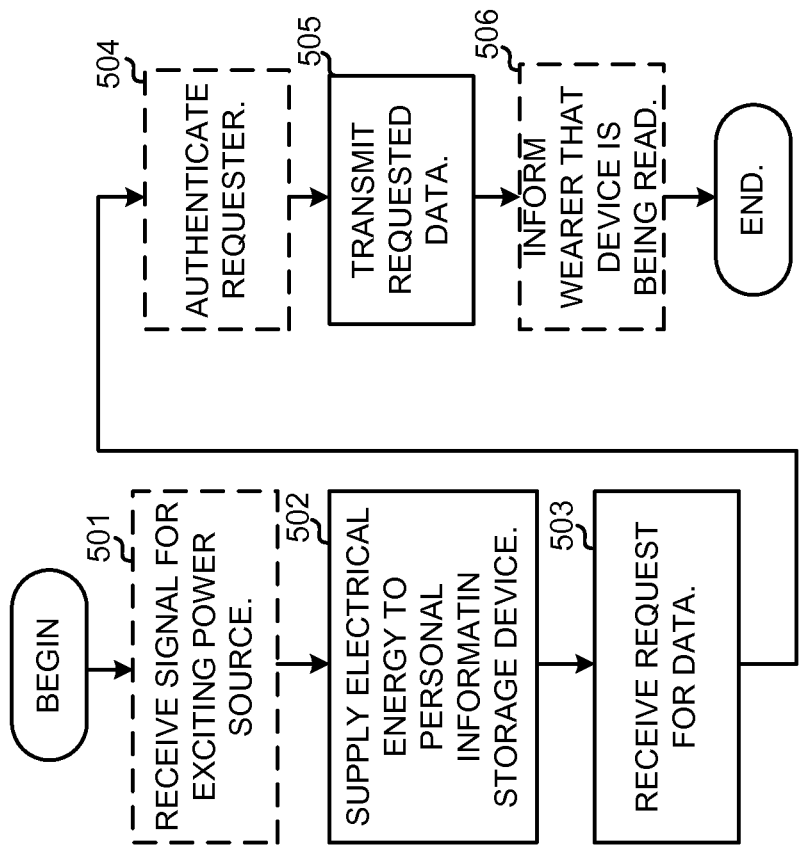
FIG. 5 is a flow chart illustrating exemplary operations of a personal information storage device when outputting data read from a data storage component.

FIG. 5 is a flow chart illustrating exemplary operations of personal information storage device 300 when outputting data read from data storage component 301. In implementations in which personal information storage device 300 includes an inductor designed to generate electrical energy from received electromagnetic energy, these operations may begin by receiving an excitation signal from external reader device 420 (act 501). In other implementations, in which power source 302 is, for example, a battery, this act may not be implemented. Power source 302 may supply electrical energy to the other components of personal information storage device 300 (act 502).

External reader 420 may transmit a request for data which may be received by personal information storage device 300 (act 503). The request may be a wireless request that is received by transceiver 303. Optionally, in implementations in which security or user privacy is an issue, the request may be authenticated to ensure that the entity reading the data is an authorized entity (act 504). Techniques for authenticating entities are described in more detail below. Control circuitry 304 may then read the requested data from data storage component 301 and transmit the data to reader 420 via transceiver 303 (act 505).

Personal information storage device 300 may optionally be configured to, in some manner, inform its user when it is being read (act 506). This act can be performed in a number of different ways depending on the particular implementation of device 300. For example, personal information storage device 300 may be designed to vibrate slightly or emit an audible sound. Ideally, personal information storage device 300 informs its user that it is being read in an unobtrusive yet noticeable manner.

Figure 6:
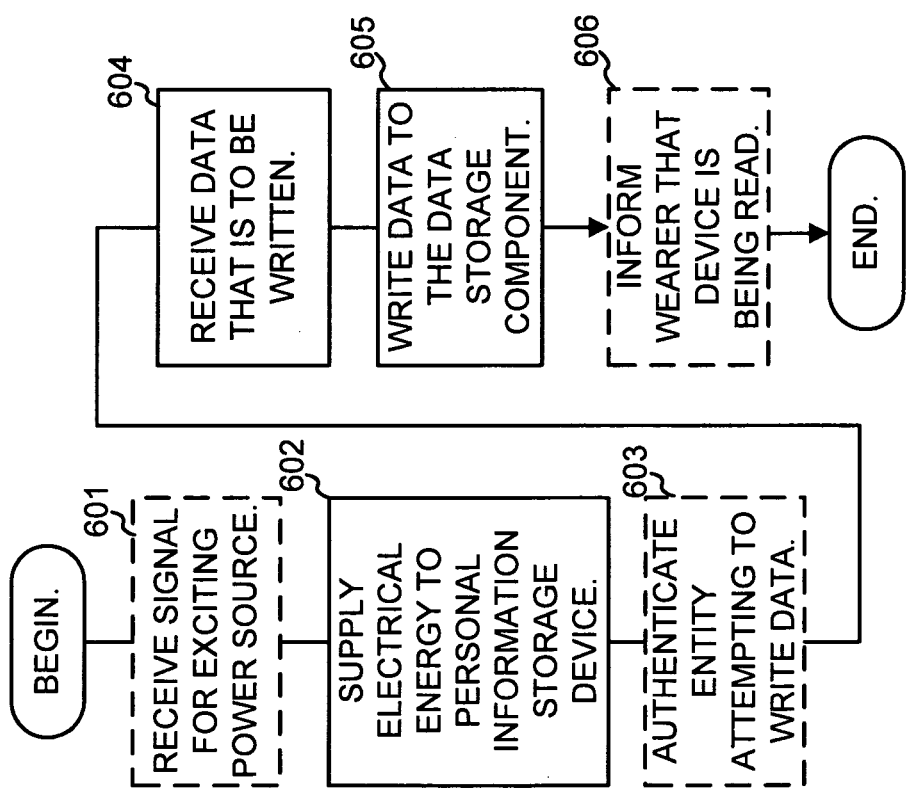
FIG. 6 is a flow chart illustrating exemplary operations of a personal information storage device when writing information to the data storage component.

FIG. 6 is a flow chart illustrating exemplary operations of personal information storage device 300 when writing information to data storage component 301. As was previously mentioned, in some implementations, personal information storage device 300 may be a read-only device. In these implementations, the acts shown in FIG. 6 are not applicable.

To begin, in implementations in which personal information storage device 300 is an inductor designed to generate electrical energy from received electromagnetic energy, these operations may begin by receiving an excitation signal from external reader 420 (act 601). In other implementations, in which power source 302 includes, for example, a battery, this act may not be implemented. Power source 302 may supply electrical energy to the other components of personal information storage device 300 (act 602).

The entity attempting to write the information may optionally be authenticated (act 603). Data to be written may then be received via transceiver 303 (act 604). Control circuitry 304 may then write the data to data storage 301 (act 605). The user may optionally be informed that data is being written in a manner similar to the informing performed in act 506 (act 606).

Applications of Personal Information Storage Device 300

A variety of types of information may be stored and retrieved from personal information storage device 300. Medical information of the user could be stored in device 300. For example, the complete medical history of the wearer may be stored in information storage device 300. Medical practitioners may update the user's medical history after each visit to the doctor. Accordingly, the complete medical history of the user can always be available to medical practitioners providing medical services to the wearer.

In other implementations, instead of a complete medical history, personal information storage device 300 may be used to store a limited set of medical information. For example, "emergency" medical information such as allergies, prescriptions, medical warnings (e.g., past history of coronary problems) could be stored. Additionally, family or emergency contact information, such as the contact information of family members, doctors, etc., could be stored. Prescription information, in particular, instead of being stored as a simple list of prescriptions, may be stored as an authenticated electronic prescription that may be read and filled by drug stores. In some implementations, control circuitry 303 may also be configured to monitor the prescription data and reminding the wearer, such as by, for example, vibrating or making an audible sound, when it is time to take a drug or otherwise act on a prescription.

Financial information may also be stored in personal information storage device 300. For example, social security numbers, bank account numbers, credit card numbers, or other account numbers may be stored in personal information storage device 300. To purchase items at retail stores or otherwise access their financial information, the user may simply stand near an appropriate reader, which may be configured to automatically read the appropriate account information.

Other useful information, in addition to financial and medical information, may be stored in personal information storage device 300. Examples include a vehicle's identification number (VIN), insurance policy numbers, phone numbers, fingerprints, blood types, electrocardiogram (EKG) data, electroencephalogram (EEG) data, and DNA data.

Authentication Of Personal Information Storage Device 300

It can be appreciated that much of the personal information stored in device 300 may be "sensitive" information that should only be read by authorized entities. As discussed above, this may be implemented through an authentication procedure performed during reading or writing of data with personal information storage device 300.

Figure 7:
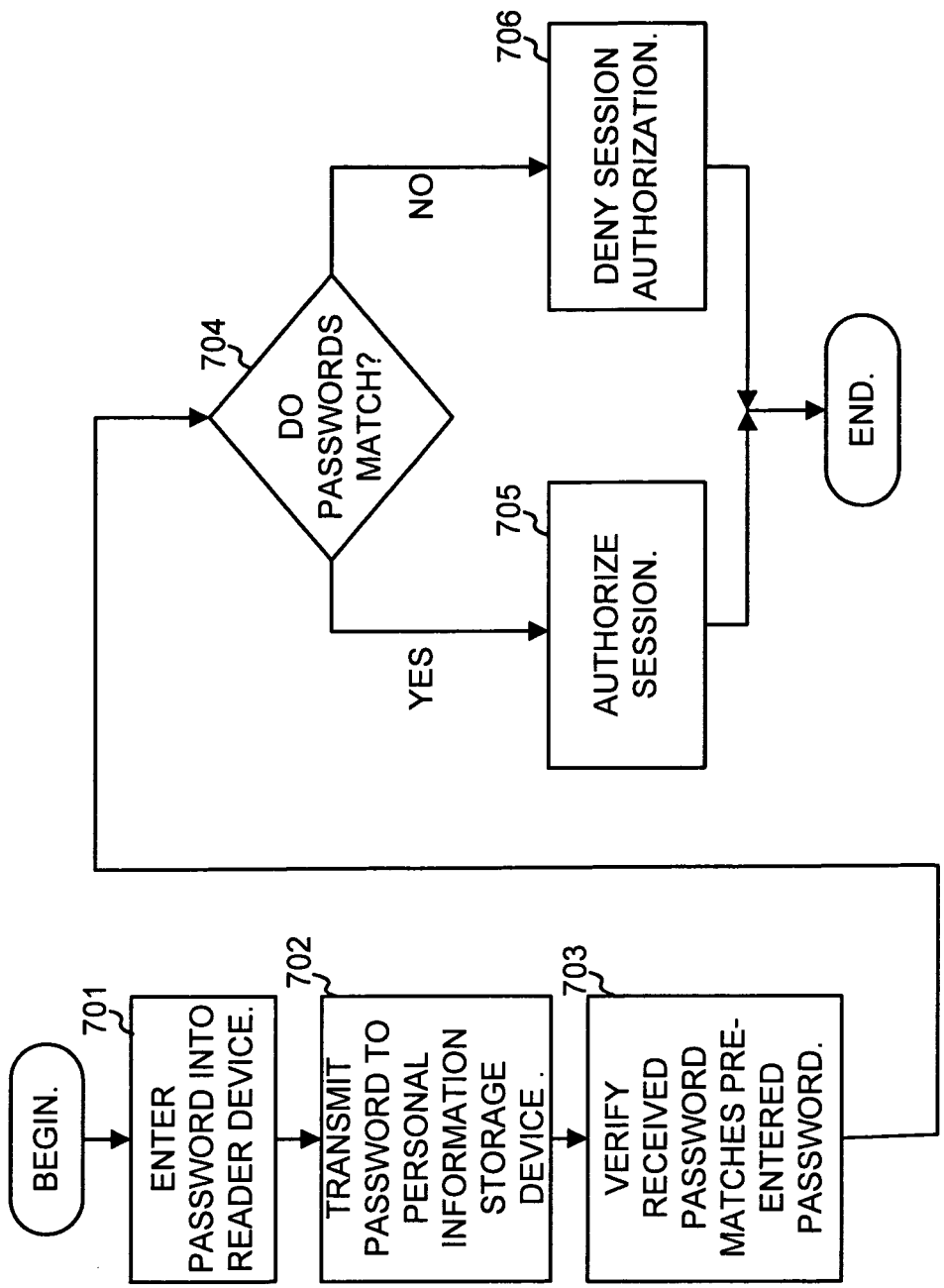
FIG. 7 is a flowchart illustrating exemplary operations for authenticating reading devices attempting to access personal information.

FIG. 7 is a flowchart illustrating exemplary operations for authenticating reading devices attempting to access personal information stored in device 300. The operations of FIG. 7 are based on authentication using a password. Password based security may be appropriate in situations such as when the wearer would like to give express permission before data is transferred from the device, such as before transferring financial information to a retailer. The user may be able to occasionally change the password.

A password may initially be stored in data storage component 301. The password may, for example, represent a series of alpha-numeric characters that were pre-entered by the wearer. When the wearer is ready to authorize the transfer of data from device 300, the wearer may enter the password into a reader device, such as reader device 420 (act 701). The reader device may include, for example, a keypad through which the user enters the password. Reader device 420 may transmit the password to personal information storage device 300 (act 702). Control circuitry 304 may then verify that the password entered by the user matches the pre-stored version of the password (act 703). If the passwords match, the session is determined to be an authorized session (acts 704 and 705). Control circuitry 304 may thus allow future data requests for protected data in storage component 301. When, however, the passwords do not match, session authorization is denied, and access to protected data in data storage component 301 will not be allowed (acts 704 and 706).

The password protection described above may be applied to all the user data in data storage component 301 or to select portions of the data in data storage component 301. For example, certain data in data storage component 301 may be deemed to be non-sensitive information that personal information stored in device 300 may transmit to any requesting device, while other data in data storage component 301 may be password protected. For example, emergency contact information and emergency medical information may be classified as non-sensitive information, while financial data and other medical information may be classified as sensitive information.

Figure 8:
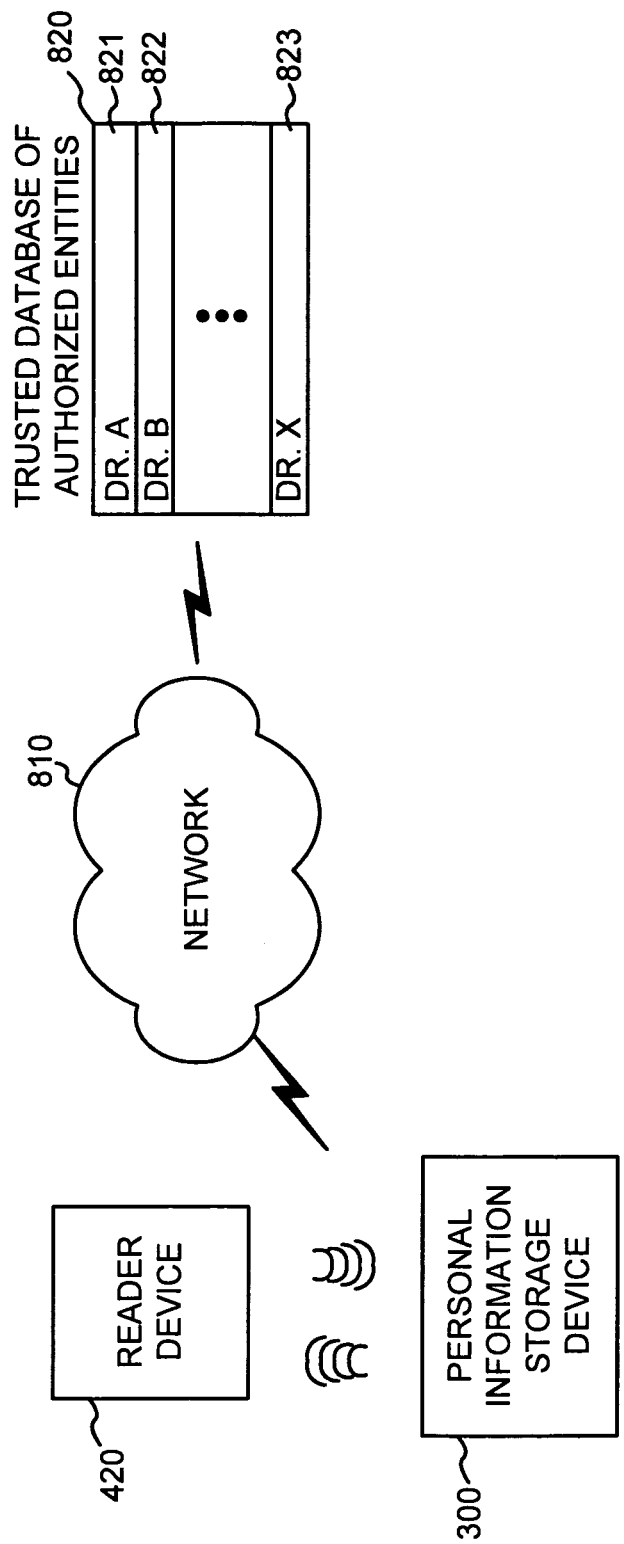
FIG. 8 is a diagram illustrating an exemplary system for authorizing users.

Password protection may not be ideal in all situations. For example, the wearer may not wish to password protect emergency medical information but may nevertheless wish to keep such information secure from non-authorized users, such as non-medical personnel. FIG. 8 is a diagram illustrating an exemplary system 800 for authorizing users.

As shown, system 800 includes a network 810 coupled to a trusted database 820. Reader device 420 may connect to network 810. Network 810 may include a local area network (LAN), a wide area network (WAN), a telephone network, such as the Public Switched Telephone Network (PSTN), an intranet, the Internet, or a combination of networks.

Trusted database 820 may include a number of entries of authorized entities. Each entry, shown as entries 821, 822, and 823, may correspond to an entity that has been pre-authorized to access information in personal information storage device 300. For example, trusted database 820 may be maintained by a trusted medical organization and store entries corresponding to licensed doctors or other medical personal. Before personal information storage device 300 will allow medical records related information to be read from data storage component 301, it may access database 820 to determine whether the entity requesting access is authorized.

Figure 9:
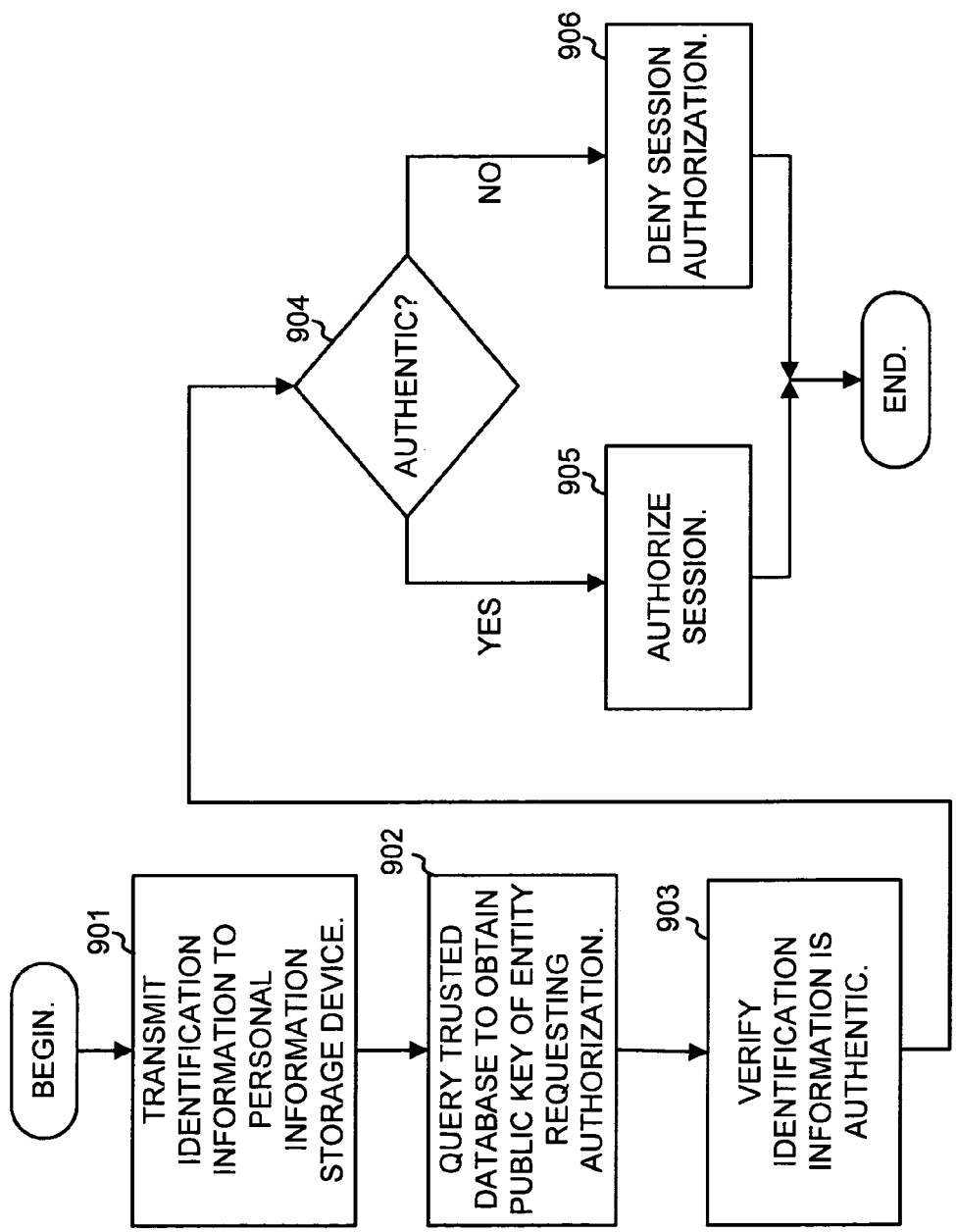
FIG. 9 is a flow chart illustrating exemplary operations for authorizing users in the system of FIG. 8.

FIG. 9 is a flow chart illustrating exemplary operations for authorizing an entity using trusted database 820. An entity, such as a doctor or other medical professional, wishing to gain authorized access to data storage component 301, may begin by transmitting data that identifies the entity from reader device 420 to personal information storage device 300 (act 901). In one implementation, the identifying data may be a digital signature generated pursuant to public key encryption techniques. As is known in the art, such digital signatures may be encrypted with the private key of the entity. Personal information storage device 300 may then query trusted database 820 to obtain the corresponding public key of the entity (act 902). With the public key received from database 820, personal information storage device 300 may verify that the signature is authentic (act 903). If the signature is authentic, personal information storage device 300 may authorize reader device 420 to access its protected data (acts 904 and 905). Otherwise, access to the protected data may be denied (acts 904 and 906).

CONCLUSION

As described above, personal information storage devices were described that enable their wearers to conveniently and unobtrusively store personal information. The personal information can include emergency information and other personal information. Secure access features were described that allow the wearers to control the entities that are able to access their personal information.

It will be apparent to one of ordinary skill in the art that aspects of the invention, as described above, may be implemented in many different forms of software, firmware, and hardware in the implementations illustrated in the figures. The actual software code or specialized control hardware used to implement aspects consistent with the invention is not limiting of the invention. Thus, the operation and behavior of the aspects were described without reference to the specific software code—it being understood that a person of ordinary skill in the art would be able to design software and control hardware to implement the aspects based on the description herein.

The foregoing description of preferred embodiments of the invention provides illustration and description, but is not intended to be exhaustive or to limit the invention to the precise form disclosed. Modifications and variations are possible in light of the above teachings or may be acquired from practice of the invention. For example, although many of the operations described above were described in a particular order, many of the operations are amenable to being performed simultaneously or in different orders.

No element, act, or instruction used in the present application should be construed as critical or essential to the invention unless explicitly described as such. Also, as used herein, the article "a" is intended to potentially allow for one or more items. Where only one item is intended, the term "one" or similar language is used. Further, the phrase "based on" is intended to mean "based, at least in part, on" unless explicitly stated otherwise. The scope of the invention is defined by the claims and their equivalents.

What is claimed:

1. An information storage device designed to be semi-permanently attached to a wearer, the device comprising:
    an outer casing configured to be compatible with long term contact with a human body;
    a data storage component located within the outer casing and configured to store information of the wearer;
    a transceiver located within the outer casing and configured to communicate with an external device;
    a power source including an inductor configured to generate power when in presence of electromagnetic radiation received from a source external to the human body, wherein the inductor is configured to generate power for the data storage component and the transceiver; and
    control circuitry configured to write and read the information of the wearer to and from the data storage component,
        wherein the transceiver is configured to receive the information of the wearer from the external device and the control circuitry is configured to write the information of the wearer to the data storage component,
        wherein the control circuitry configured to read the information of the wearer from the data storage component the transceiver is configured to transmit the information of the wearer to the external device using the transceiver, and
        wherein the information storage device is configured to inform the wearer, by vibrating or emitting an audible sound and in response to the information being accessed by the external device, that the information stored in the device is being accessed by the external device.

2. The device of claim 1, wherein the outer casing includes material compatible with human tissue and is configured to be subcutaneously inserted into the wearer.

3. The device of claim 2, wherein the outer casing includes a smooth material that is an oblong or rounded shape.

4. The device of claim 1, wherein the outer casing is configured in a shape of a false tooth or crown.

5. The device of claim 1, wherein the data storage component stores a social security number associated with the wearer.

6. The device of claim 1, wherein the transceiver is configured to communicate wirelessly with the external device.

7. The device of claim 1, wherein the data storage component stores medical history information of the wearer.

8. The device of claim 1, wherein the data storage component stores contact information for a family member of the wearer.

9. The device of claim 1, wherein the data storage component stores emergency contact information of the wearer.

10. The device of claim 1, wherein the data storage component stores an electronic medical prescription associated with the wearer and capable of being digitally authenticated.

11. The device of claim 1, wherein the data storage component stores financial information of the wearer.

12. The device of claim 1, wherein the data storage component stores a blood type of the wearer.

13. A system comprising:
    a personal information storage device comprising:
    a data storage component configured to store information associated with a wearer;
    a transceiver configured to communicate with an external reader device; and control circuitry to authenticate the external reader device as authorized to access the information associated with the wearer, wherein the control circuitry authenticates the external reader device based on information provided to the external reader device by the wearer, wherein the transceiver is configured to send the information associated with the wearer to the external reader device when the control circuitry authenticates the external reader device, and wherein the personal information storage device is a subcutaneous device or as a device disposed within an oral cavity of the wearer; and a power source including an inductor configured to generate power when in presence of electromagnetic radiation received from a source external to a human body, wherein the inductor provides power to the information storage device including the transceiver and the storage component, wherein the personal information storage device is configured to inform the wearer, by vibrating or emitting an audible sound and in response to the information being accessed, that the information stored in the information storage device is being accessed.

14. The system of claim 13, wherein the information associated with the wearer includes a social security number associated with the wearer.

15. The system of claim 13, further comprising the external reader device, wherein the external reader device includes an input device to receive the information from the wearer for authentication.

16. The system of claim 15, wherein the transceiver is configured to receive data from the external reader and wherein the control circuitry is further configured to write the received data to the data storage component when the control circuitry authenticates the external reader.

17. The system of claim 13, wherein the external reader device includes a point-of-sale terminal, wherein the information associated with the wearer includes a credit card number, and the information from the wearer for authentication includes a password or a personal identification number (PIN).

18. The system of claim 13, wherein the information associated with the wearer includes information indicating medications to which the wearer is allergic.

19. The system of claim 13, wherein the data storage component stores medical history information of the wearer.

20. The system of claim 13, wherein the data storage component stores emergency medical information of the wearer.

21. The system of claim 13, wherein the data storage component stores emergency contact information of the wearer.

22. The system of claim 13, wherein the data storage component stores medical prescription information associated with the wearer, the system further comprising:

the reader device, wherein the reader device receives the medical prescription information for filling a medical prescription for the wearer at a drug store.

23. The system of claim 13, wherein the data storage component stores financial information relating to the wearer.

24. A method of providing information from a storage device attached to a wearer, the method comprising:

wirelessly receiving, by a transceiver in the storage device attached to the wearer, and from a reader device not attached to the wearer, a request for data;

wirelessly receiving, by the transceiver in the storage device attached to the wearer, information for the storage device to authenticate the request as being from a device authorized to access data in the storage device, authenticating the request, wherein the information for the storage device to authenticate the request includes information provided to the reader device by the wearer, or wherein the information for the storage device to authenticate the request includes a digital signature encrypted with a private key associated with an authorized entity;

wirelessly transmitting, by the transceiver, the requested data to the reader device from the storage device when the storage device authenticates the request, wherein the storage device attached to the wearer is a subcutaneous device or as a device disposed within an oral cavity of the wearer;

wirelessly receiving electromagnetic radiation, in an inductor in the storage device, from the reader device, wherein the inductor is configured to generate power when in the presence of the electromagnetic radiation to power the transceiver in the storage device; and informing the wearer, in response to the information being accessed, that the information stored in the storage device is being accessed, by vibrating emitting an audible sound.

25. The method of claim 24, wherein receiving the information allowing the storage device to authenticate the request includes wirelessly receiving, in the storage device attached to the wearer, a password or personal identification number (PIN) from the reader device, wherein the wearer entered the password or PIN into the reader device; and wherein authenticating the reader device includes determining whether the password or personal identification number matches a pre-stored version of the password.

26. The method of claim 25, wherein the reader device includes a point-of-sale terminal and the requested data transmitted to the reader device includes a financial account number associated with the wearer.

27. The method of claim 24, wherein authenticating the request includes:

sending a query from the storage device to a trusted database to locate information relating to an entity associated with the request; and determining whether the entity associated with the request is authentic based on the query of the trusted database.

28. The method of claim 24, wherein the requested data transmitted to the reader device includes medical history information of the wearer.

29. The method of claim 24, wherein the requested data transmitted to the reader device includes emergency medical information of the wearer.

30. The method of claim 24, wherein the requested data transmitted to the reader device includes contact information of a family member of the wearer.

31. The method of claim 24, wherein the requested data transmitted to the reader device includes medical prescription information of the wearer for filling a medical prescription for the wearer at a drug store.

32. The method of claim 24, wherein the information from the storage device includes at least one of a vehicle identification number (VIN), an insurance policy number, a fingerprint, blood type, electrocardiogram (EKG) data, electroencephalogram (EEG) data, or DNA data.

* * * * *